United States Patent [19]

Corby et al.

[11] Patent Number: 5,514,342

[45] Date of Patent: May 7, 1996

[54] MEDICAL INSTRUMENT SHIELDED CONTAINER FOR MICROWAVE STERILIZATION

[75] Inventors: Kenneth D. Corby, Rochester; Francisco Chiarilli, Spencerport; David E. Foeller, Batavia; Fugui He, Penfield; Jacob M. Shmois, Rochester; Peter J. Harissis, Rush; Mary Beth M. Allen; Mary-Irene E. Condo, both of Rochester, all of N.Y.

[73] Assignee: Eastman Kodak Company, Rochester, N.Y.

[21] Appl. No.: 483,617

[22] Filed: Jun. 7, 1995

Related U.S. Application Data

[62] Division of Ser. No. 222,211, Apr. 4, 1994, Pat. No. 5,464,589.

[51] Int. Cl.[6] ........................................ A61L 9/12
[52] U.S. Cl. .............................. 422/102; 422/21; 422/26; 422/103; 220/307
[58] Field of Search ........................ 422/20, 26, 28, 422/102, 294, 305, 103–104; 220/306–307, 324

[56] References Cited

U.S. PATENT DOCUMENTS

| | | | |
|---|---|---|---|
| 1,753,631 | 4/1930 | Walters | 220/307 |
| 4,201,311 | 5/1980 | Underwood | 220/307 |
| 4,317,017 | 2/1982 | Bowen | 219/10.55 |
| 4,400,357 | 8/1983 | Hohmann | 422/297 |
| 4,840,286 | 6/1989 | Herberling et al. | 220/307 |
| 5,248,478 | 9/1993 | Kutner et al. | 422/21 |

FOREIGN PATENT DOCUMENTS

93/18798  9/1993  WIPO .

*Primary Examiner*—Lyle A. Alexander
*Attorney, Agent, or Firm*—Robert Luke Walker

[57] ABSTRACT

A container for sterilizing objects contained in a pouch (66) is provided with shield portions (30, 32) having a wiper fingers (42) located on at least one side edge portion (44) of a peripheral edge (40) of one of the shield portions (30, 32). The wiper fingers (42) insure that metal-to-metal contact is maintained between the shield portions (30, 32) during sterilization. The pouch (66) is constructed from two sheets of a laminate materials, and includes an instrument retaining portion (68) and a fluid retaining portion (70). A water pillow (80) that bursts during sterilization is provided within the fluid retaining portion (70). Alternatively, a temporary seal (86) that bursts or opens during sterilization is provided within the fluid retaining portion (70) to prevent the premature transfer of a sterilization fluid contained in the fluid retaining portion (70) to the instrument retaining portion (68).

13 Claims, 8 Drawing Sheets

MEDICAL INSTRUMENT SHIELDED CONTAINER FOR MICROWAVE STERILIZATION

This is a Divisional of application Ser. No. 08/222,211, filed 04 April 1994, now U.S. Pat. No. 5,464,589.

FIELD OF THE INVENTION

The invention relates to a shield, a pouch and the container using them, for sterilizing medical instruments by steaming them in a microwave oven.

BACKGROUND OF THE INVENTION

Devices are known for microwave-sterilization of medical instruments such as dental instruments—for example, those taught in PCT WO 93/18798. Typically such a design uses a pouch sealed with the instruments inside, which is positioned with at least the instrument portion of the pouch between two shield portions, the entire combination being locked between two portions, preferably hinged together, of a plastic cassette. In any such device, an important component is the noted microwave shield that is disposed around the metal instruments, preferably using two clam-shell portions that come into contact at mating "faces" when closed to provide a shielded chamber inside. As is well known, the shield prevents the transmission of microwave radiation to the metal instruments, since the unrestricted transmission of such would cause arcing of the instruments and surface damage. Another example of such shielding is taught in U.S. Pat. No. 5,248,478, wherein two small hemispherical metal portions are used to shield contact lenses rather than medical instruments.

We have discovered that merely surrounding instruments with a "closed" metal shield having "choke" edges in facing contact is not sufficient to prevent all arcing within the chamber formed by the shield. There are several reasons why a choke created by nominally contacting faces of two shield portions is not enough, but in all cases it is primarily due to the fact that the contact between the shield facing portions cannot be sufficiently maintained during microwaving. Specifically we have discovered that a) the expansion pressure of the sterilizing steam forces the "contacting" faces of the 2 shield portions to gap apart, and b) the build-up of dirt, dust or other particles in the "contacting" faces prevents the uniform contact in the first place, upon repeated use.

Such gap formation, though nominally small, leads to several detrimental results: First, the large sizes needed for medical instruments makes this case different from a small shield of the type described in U.S. Pat. No. 5,248,478 discussed above, in that unequal electrical potentials are created in the two shield portions due to uneven microwave energy distributions in the oven. These in turn cannot be equilibrated between the shield portions due to the gap, and arcing across the chamber inside the shields can occur. Second, the gap "leaks" microwave energy into the chamber, sufficient to create the risk of arcing between metallic tools being sterilized. Third, the gap induces arcing between the "contacting" faces of the shield portions, which due to the proximity of the sealed pouch inside the shielded chambers containing the tools, damages the pouch seal.

The difficulty then, prior to this invention, has been to construct a shield of significant size in two closable, contacting portions which, when closed, maintains sufficient contact during microwaving as to provide the effective electrical equilibration between shield portions that is necessary to neutralize uneven electrical potentials that tend to build up, eliminate "leaking" of microwave energy into the shielded chamber, and prevent arcing between the contacting faces, now gapped apart under pressure.

SUMMARY OF THE INVENTION

We have designed a shield, a pouch and a container using the same, which overcome the above-noted problems.

More specifically, in accord with one aspect of the invention, there is provided a container for microwave-sterilizing metal instruments by heating a sterilizing fluid such as distilled water to a boil, the container comprising a non-metallic housing, a source of water in the housing, a shielded chamber comprising two metallic shield portions that contact each other to enclose a metal instrument, and passageways into and out of the chamber for fluid flow, each of the shield portions having a preformed peripheral side edge. The container is improved in that at least one shield portion is provided with means along most of its side edge for wiping along and into a corresponding edge of the other of the shield portions to ensure an effective electrical contact, even in the presence of a gap between the shield portions.

In accord with another aspect of the invention, there is provided a shield for use in a microwave container for steam-sterilizing a metal instrument, the shield comprising a first and a second shield portion each having a domed center and a peripheral side edge around the domed center, one of the shield portions being provided with means along most of its side edge for wiping along and into a corresponding edge of the other of the shield portions to ensure an effective electrical contact, even in the presence of a gap between the shield portions.

In accord with another aspect of the invention, a sealable pouch for sterilizing instruments is provided that includes a first laminate sheet sealed to a second laminate along first, second and third edges, and means for defining a fluid retaining portion and an instrument retaining portion. The means for defining the fluid retaining portion and the instrument retaining portion preferably comprises a central seal located between the first and second sealed edges. The central seal defines at least one steam/condensate slot that provides a passage between the fluid retaining portion and the instrument retaining portion. A water pillow is located in the fluid retaining portion. Alternatively, a seal is located in the steam/condensate slot to retain a sterilization fluid in the fluid retaining portion. The seal can also be employed between the first and second sealed edges at a location before the central seal.

Accordingly, it is an advantageous feature of the invention that a shield, pouch and/or a container for the shield are provided for microwave-sterilizing of metal instruments, in which the shield retains its shielding effect even when internal pressure causes the shield portions to gap apart slightly.

It is a related advantageous feature of the invention that such a shield and its container are provided wherein the shield is effective after repeated uses, even when dirt or other particles find their way into place between the nominally contacting portions of the shield.

A further advantageous feature of the invention is that the a central seal of the pouch aids in the seating and sealing of the pouch in the container.

Other advantageous features will become apparent upon reference to the Description of the Preferred Embodiments, when read in light of the attached drawings.

BRIEF DESCRIPTION OF THE DRAWINGS

The invention will be described in greater detail with reference to the attached drawings, wherein.

DESCRIPTION OF THE PREFERRED EMBODIMENTS

The invention is described in connection with certain preferred embodiments, in which the shield of the invention is disposed within a container of a preferred type, using a preferred pouch to contain certain preferred dental instruments and a source of water, which is disposed in a microwave oven, the shield being manufactured from certain preferred materials. In addition, the invention is useful regardless of the nature or design of a) the container; b) the pouch, c) the instruments being sterilized, d) the oven used, or e) the materials of the shield construction, so long as the feature of maintaining good electrical contact between opposed side edges of each shield portion is obtained even when gaps are caused to occur between them.

Figure 1:
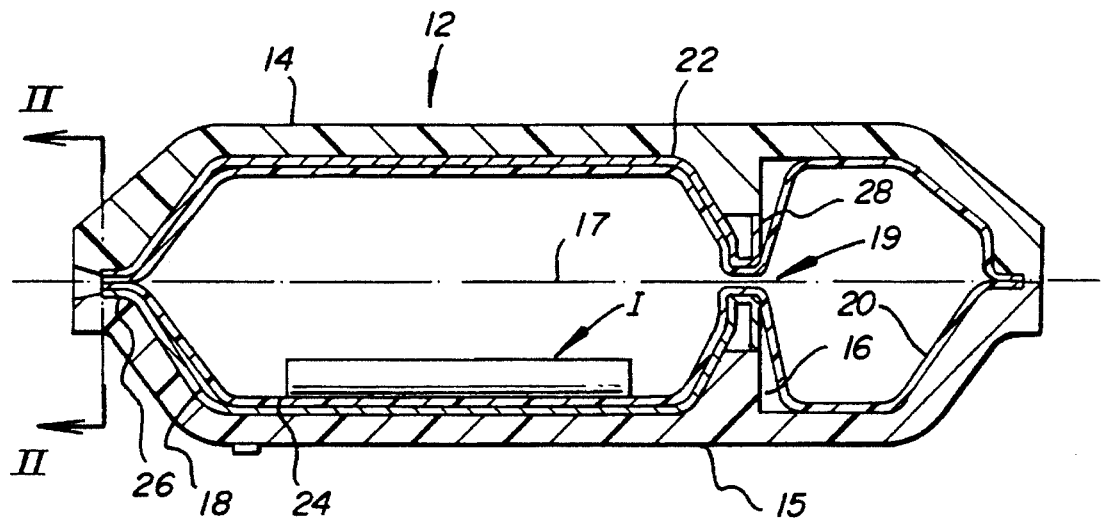
FIG. 1 is an elevational view in section of a prior art container and shield which cannot remain effective when gaping occurs.

The problem addressed and solved of the invention is best illustrated by reference to the prior art container and shield described in PCT WO 93/18798 and shown here as FIGS. 1 and 2. That container 12 features two housing portions 14 and 15 hinged along one edge, for example the edge represented by junction 17, and clamped together along the opposite edge, not seen. Each portion 14 and 15 has two concavities 16 and 18, which together (when portions 14 and 15 are closed) provide a steam-generating chamber and a shielded chamber for dental instruments I, respectively. Both instruments I and a source of water (not shown) are preferably included within a sealed plastic pouch 20 which occupies both concavities 16 and 18. A passageway 19 is provided between concavities 16 and 18, for steam. To shield only instruments I, and not water placed in concavities 16, two shield portions 22 and 24 are mounted within the container, each in one of the concavities 18. Each portion 22 and 24 is dome-shaped to match the concavity of 18, and has a peripheral side edge 26 that is flanged upwardly at 28 adjacent passageway 19, but is otherwise flat to parallel the flat portion of the opposite side edge of the opposite shield portion, shown at the left side of FIG. 1.

Figure 2:
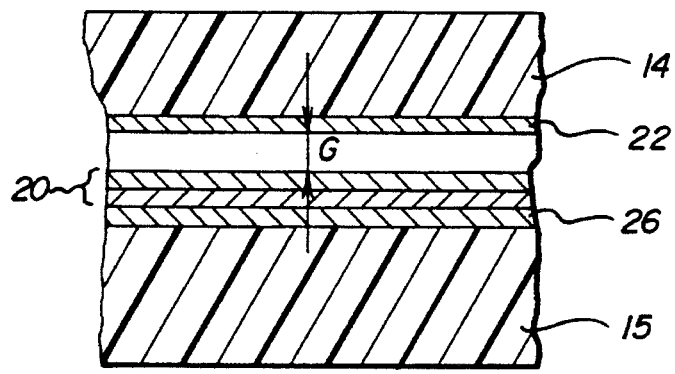
FIG. 2 is a fragmentary sectional view taken generally along the line II—II of the prior art of FIG. 1, showing the gaping.

In such a container, even the tightest closure mechanism will still result in a gap G, FIG. 2, forming between one side edge 26 and the pouch edge 30 nominally clamped by shield portions 22 and 24, when steam is generated in the container. For a container of the type shown in the aforesaid WO 93/18798, this gap is as much as 0.1 cm (40 mils). It has been further shown that this gap destroys the shielding effect of the shield portions, due to a) arcing at the side edges which tends to burn through the pouch, b) leakage of microwave energy into the compartment, and c) unequal electrical potentials developing between the shield portions. Both b) and c) tend to produce arcing across the interior of the shield portions and damage to the metal instruments inside.

Figure 3:
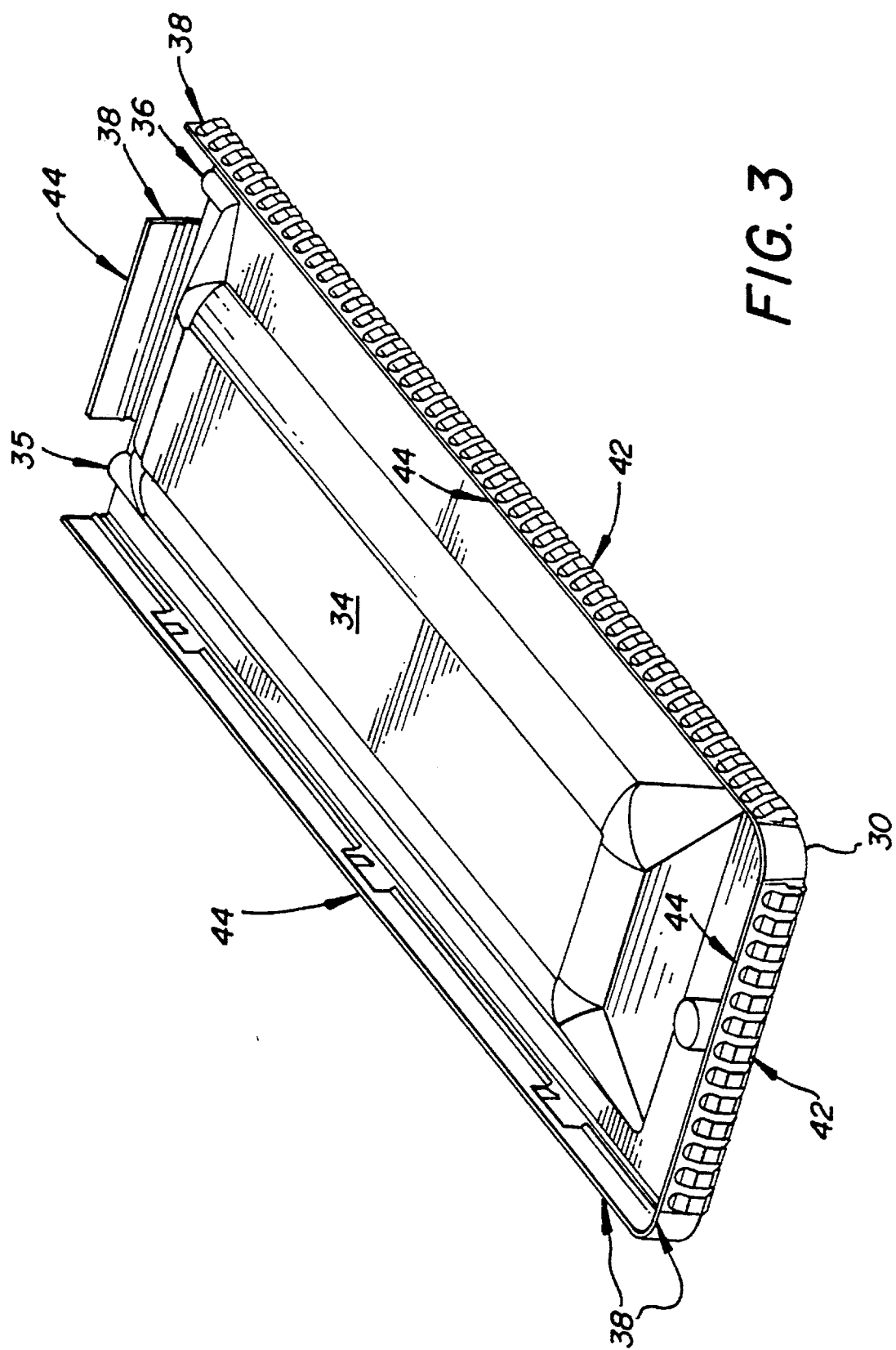
FIGS. 3 and 4 are plan views of first and second shield portions in accordance with the invention.
Figure 4:
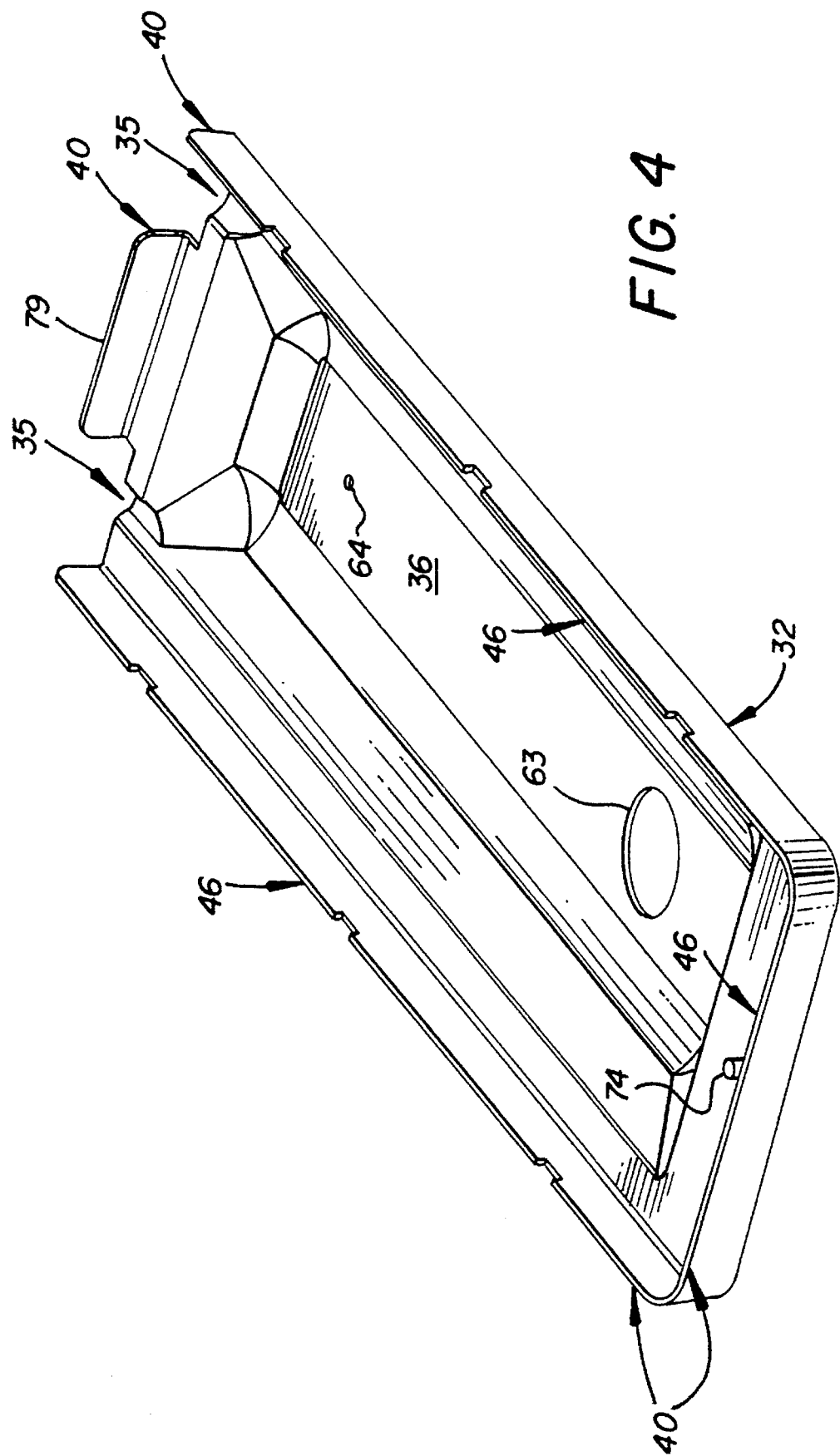

The invention solves the problem of arcing by providing a mechanism or means for maintaining metal-to-metal contact between shield portions, as the shield portions are moved apart to form a gap during the buildup of internal pressure. As shown in detail in FIGS. 3 and 4, the invention provides a shield having a first-shield portion 30 and a second shield portion 32, each having a domed center 34, 36 and a peripheral side edge 38, 40 around the domed center 34, 36. The peripheral side edge 38 of the first shield portion 30 is shaped to cooperate with the peripheral side edge 40 of the second shield portion 32 to form a microwave choke when the two shield portions 30, 32 are mated together. The shield portions 30, 32 also include at least one pre-formed liquid access aperture 35 that leads into a volume defined by the domed centers 34, 36 when the shield portions 30, 32 are mated.

In order to insure metal-to-metal contact, a plurality of flexible wiping fingers 42 are preferably disposed along three of the side edge portions 44 of the peripheral side edge 38 of the first shield portion 30, such that the wiping fingers 42 are located along at least 85% of the peripheral side edge 38. The wiping fingers 42 are biased to wipe against a corresponding side edge portion 46 of the second shield portion 32 when the shield portions 30, 32 are brought into, or removed from, contact with each other. The spring like flexible wiping fingers 42 continue to maintain metal-to-metal contact between the shield portions 30, 32, as the shield portions 30, 32 move apart, due to internal pressure as described above, for gaps as large as 0.5 cm.

Figure 5:
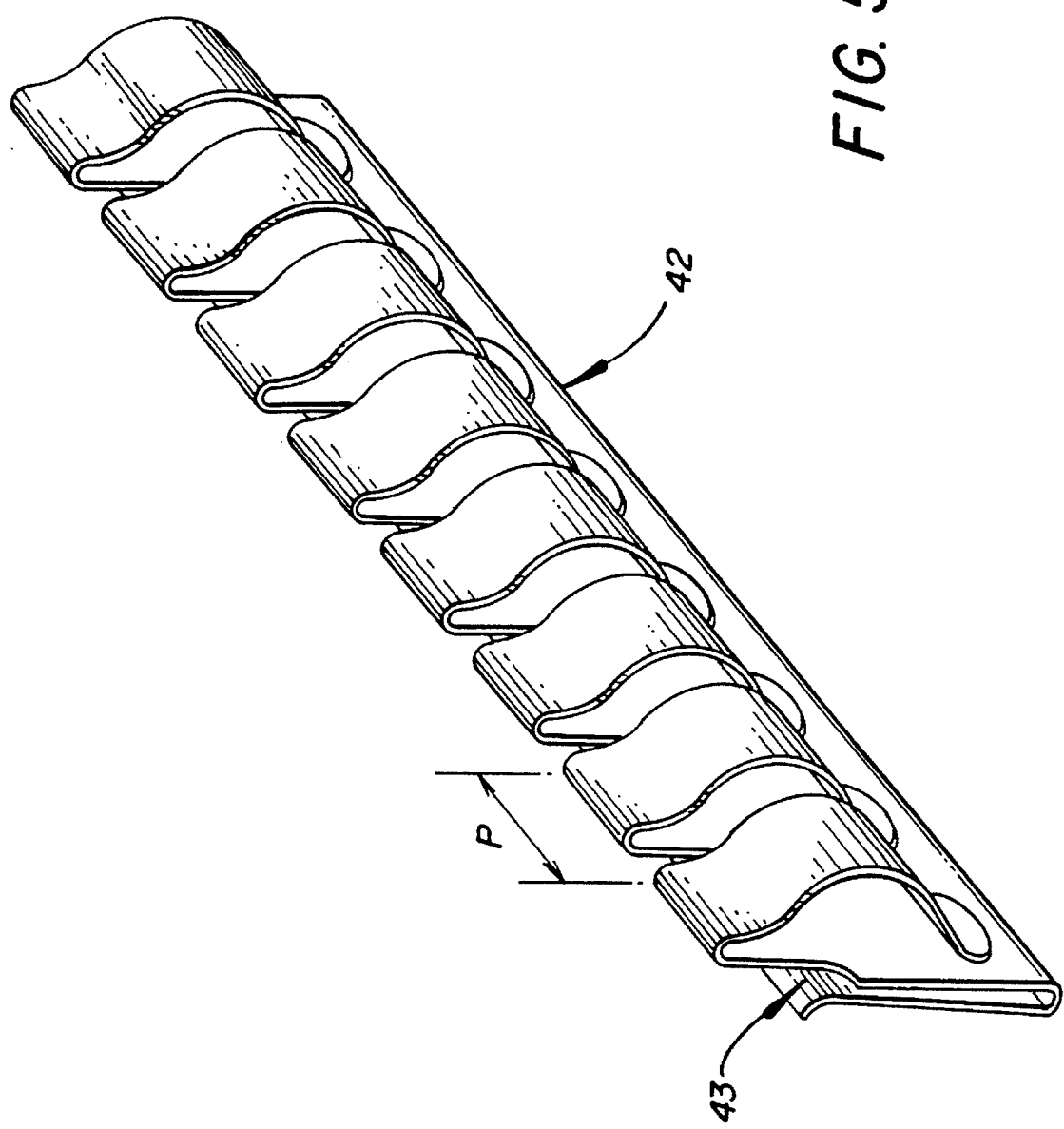
FIG. 5 illustrates a section of wiper fingers employed on at least one side edge of at least one of the first and second shield portions shown in FIGS. 3 and 4.

The wiping fingers 42 are repeated at a pitch P of 0.48 cm (see FIG. 5) along the side edge portion 44, so that metal-to-metal contact is maintained by a wiping action even in the presence of dirt. In the illustrated embodiment, the flexible wiping fingers 42 manufactured from beryllium copper, although other materials may be readily employed, and are formed by stamping and bending operations to include a "U" shaped slot 43, shown in detail in FIG. 5, that fits over the side edge portions 44 of the shield portions 30 thereby enabling the wiping fingers 42 to be clipped onto the shield portions 30 without requiring a further fastening mechanism therebetween (although one may be readily employed if so desired).

The shield portions 30, 32 are generally rectangular, with the peripheral edges 38, 40 including two pairs of parallel side edge portions 44. While the flexible wiping fingers 42 are preferably disposed along at least three of the four side edge portions 44, it is most preferably that the flexible wiping fingers 42 be disposed along all four side edge portions 44 so that at least 90% of the peripheral side edge of at least one of the shield portions is provided with the flexible wiping fingers 42.

Figure 6:
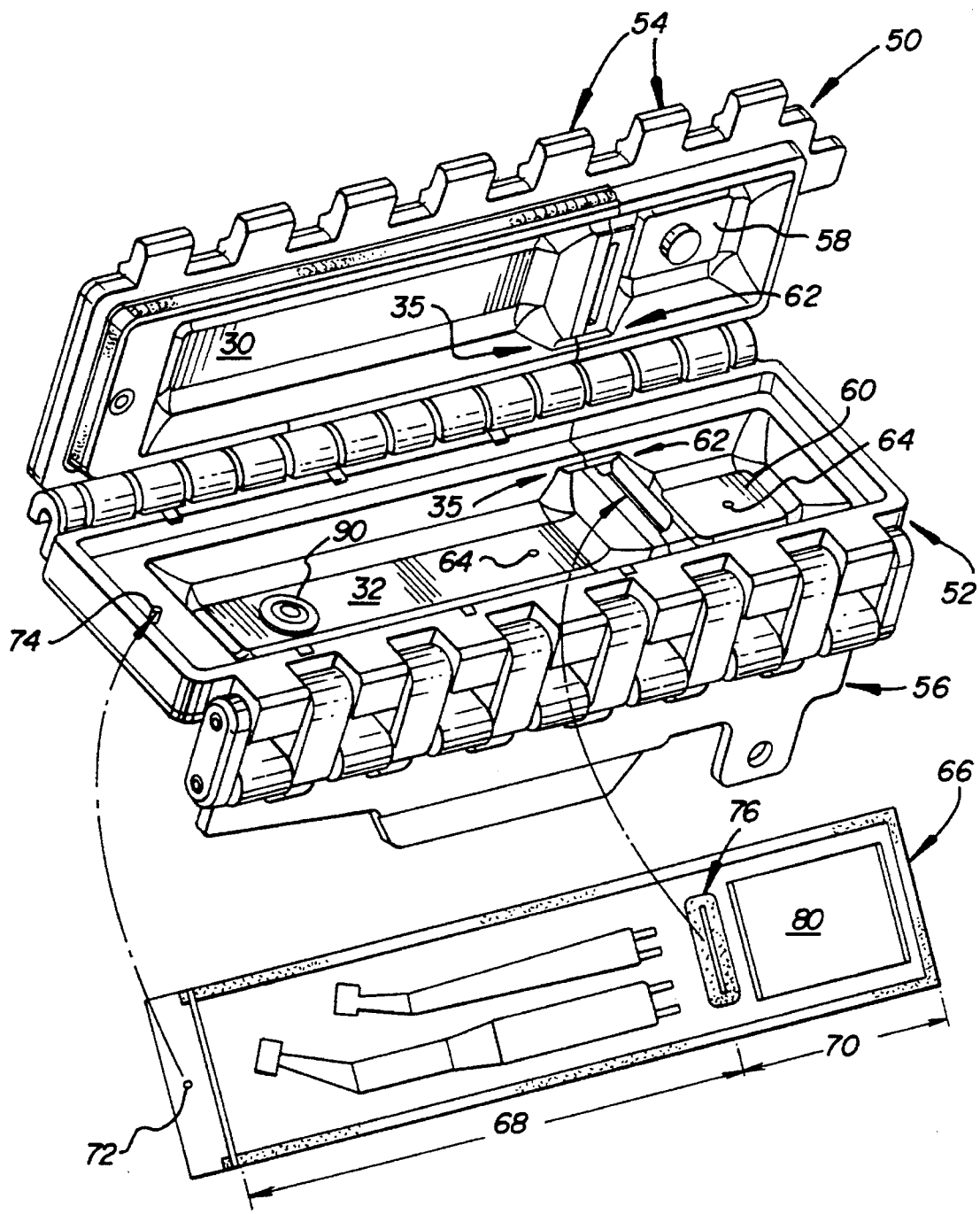
FIG. 6 is a perspective view of a container incorporating the shield portions shown in FIGS. 3 and 4.

FIG. 6 illustrates the incorporation of the shield of the invention in a container structure having an upper container portion 50 hinged to a lower container portion 52. One edge of the upper container portion 50 includes locking members 54 that cooperate with a hinged locking member 56 located on the lower container portion 52. The first and second shield portions 30, 32 are respectively located in concavities formed in the upper and lower container portions 50, 52, so that a shielded chamber is provided for Instruments to he sterilized when the contain portions 50, 52 are closed. The upper and lower container portions 50, 52 also include concavities 58 and 60, which together form a steam-generating chamber when the container portions are closed. The concavities 58, 60 include at least one livid access aperture 62 that cooperates or aligns with the livid access apertures 35 formed in the shield potions 30, 32.

The container may optionally include a temperature sensor 90 fitted in an opening 63 (FIG. 4) provided in one of the shield potions 30, 32, and a pressure relief device that operates with a pressure relief hole or passage 64 provided in one of the shield portions 30, 32 and/or the steam generating chamber 60.

In operation, the container is heated to at temperature of about 133 degrees centigrade for two minutes to achieve a 12 log kill rate of bacteria. Specifically, a pouch 66 including an instrument retaining potion 68 and a fluid retaining portion 70 is loaded into the container. The container is then placed into a microwave oven, and sterilization fluid within the fluid retaining portion 70 is vaporized by the application of microwave energy to form steam. The steam passes into the instrument retaining portion 68 in order to sterilize instruments contained therein.

Figure 7:
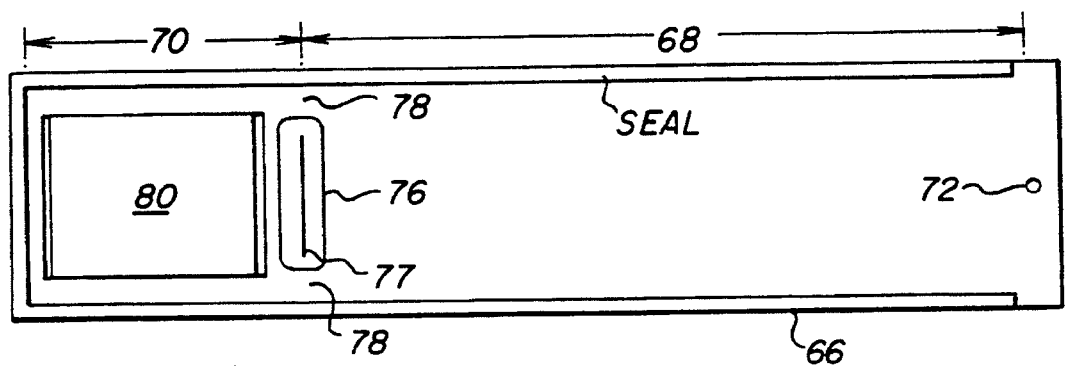
FIG. 7 is a top view of a first embodiment of a sterilization pouch.

The pouch 66 preferably includes a locating pin hole 72 located at one end thereof that aligns with a locating pin 74 provided in the container, in this case on the shield portion 32, and a central seal 76 that defines the boundary between the fluid retaining portion 70 and the instrument retaining portion 68. As shown in greater detail in FIG. 7, a slot 77 is formed in the central seal 76 to permit pouch 66 to be fitted over an upwardly extending side edge portion 79 of the shield portion 32 (FIG. 6). Steam/condensate slots 78 are located on each side of the central seal 76, and are aligned with the liquid access apertures 62, 35 when the pouch 66 is loaded in the container. The steam/condensate slots 78 permit steam to be transferred from the fluid retaining portion 70 to the instrument retaining portion 68 during a sterilization operation.

A water pillow 80 containing sterilized water is located in the fluid retaining portion 70 of the pouch 66. The water pillow 80 is formed from a standard low density polyethylene (LDPE) tube bag that is cut to the desired length sealed at one end, filled with the sterilized water, and then sealed at the other end. During a sterilization operation, the water pillow 80 ruptures due to the heat and pressure generated by the application of microwave energy, causing steam to pass through the steam/condensate slots 78 and into the instrument retaining portion 68.

Figure 8:
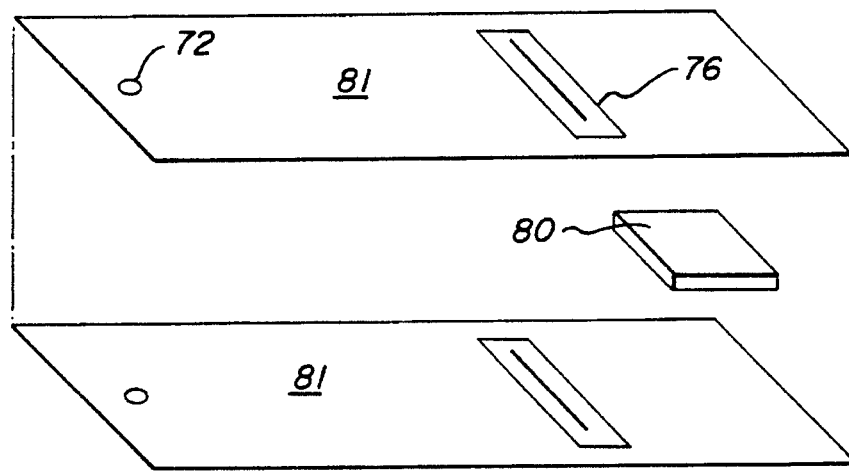
FIG. 8 illustrates the structure of the pouch illustrated in FIG. 7.
Figure 9:
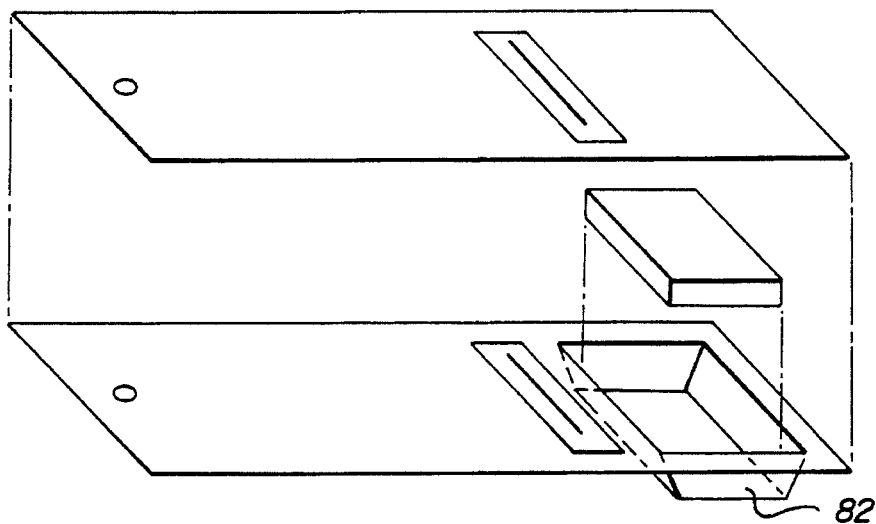
FIG. 9 is a top view of a second embodiment of a sterilization pouch.

The pouch 66 is formed by placing the water pillow 80 between two sheets 81 of a pouch material, preferably a laminate material (although non-laminates may also be employed) including a thin biaxially oriented nylon outer layer and a high temperature polypropylene inner layer as shown in FIG. 8, that are subsequently sealed on three sides and provided with the locating pin hole 72 and central seal 76. Alternatively, the laminate sheets 81 can be sealed along their lengths and provided with the locating pin hole 72 and the central seal 76 prior to the placement of the water pillow 80 within the fluid retaining portion 70 of the pouch 66. The open end of the fluid retaining portion 70 is then sealed. In order to provide room for a larger water pillow 80, one sheet of the laminate material can be provided with a thermoformed pouch or pocket 82, as shown in FIG. 9, to accommodate larger water pillows and to help maintain the edges of the pouch 66 substantially flat.

Figure 10:
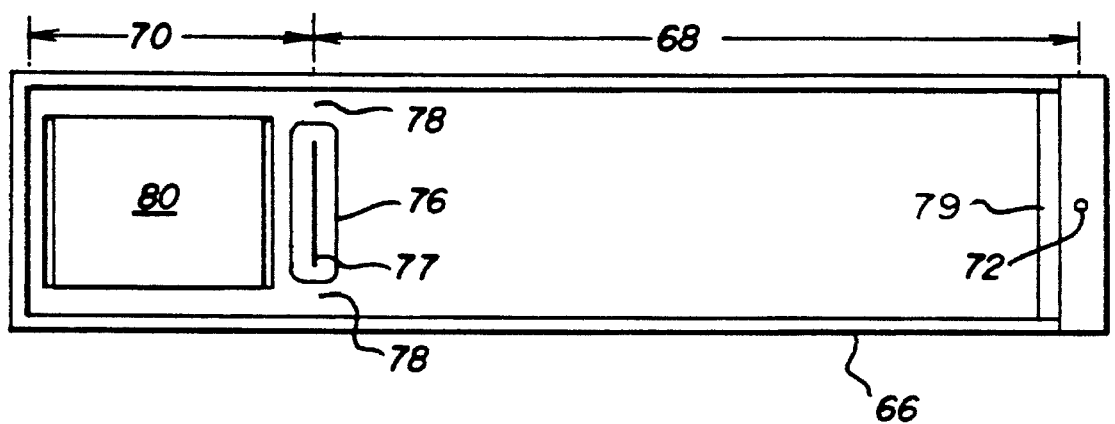
FIG. 10 is a top view of a third embodiment of a sterilization pouch.
Figure 11:
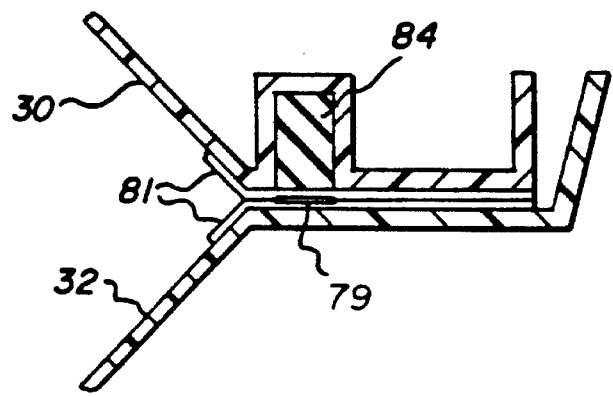
FIG. 11 is a cross-sectional view illustrating the retention of the pouch illustrated in FIG. 10 within a sterilization container.

In either method of manufacture of the pouch, the instrument retaining portion 68 remains open at one end to permit instruments to be inserted therein. The open end is subsequently sealed by the user with a standard impulse sealer such as a Model AIE-100 sealer available from the American International Electric Company. Alternatively, the pouch 66 can be provided with a self-sealing feature by coating a hot melt adhesive strip 79 onto one of the laminate sheets (See FIG. 10) prior to assembling the pouch 66. During sterilization, the adhesive strip 79 becomes soft and sticky and subsequently seals the open end of the instrument retaining portion 68 when the pouch 66 is cooled. In such a case, one of the shield portions 30, 32 is preferably provided with a gasket 84 that maintains the pressure in the instrument retaining portion 68 during the sterilization process as shown in FIG. 11.

Figure 12:
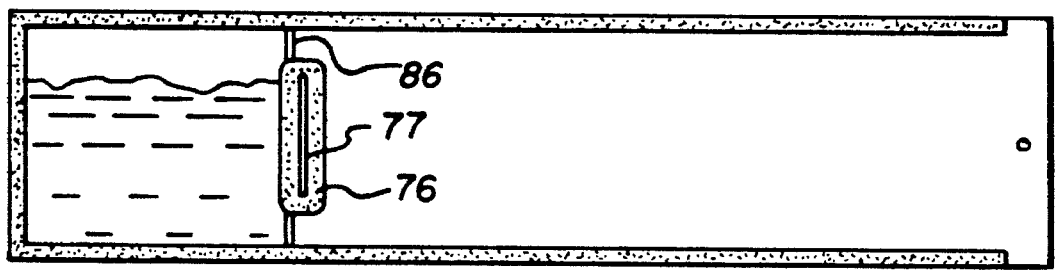
FIG. 12 is a top view of a fourth embodiment of a sterilization pouch.
Figure 13:
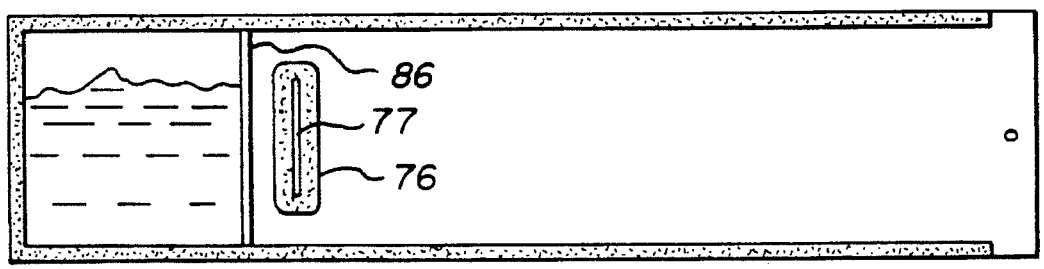
FIG. 13 is a top view of a fifth embodiment of a sterilization pouch.

The pouch 66 can be simplified by eliminating the water pillow entirely and directly filling the fluid retaining portion 70 with a sterilization fluid such as distilled water. In such a case, a mechanism or means must be provided to prevent the sterile water from prematurely flowing into the instrument retaining portion 68. For example, a temporary fluid retention seal 86, either a mechanical seal that ruptures in a manner similar to the water pillow when the appropriate heat and pressure conditions are achieved or an adhesive seal that releases under the heat and pressure of sterilization, can be provided either across the entire width of the pouch or at the steam/condensate slots 78 as shown in FIGS. 12 and 13, thereby eliminating the necessity for a separate water pillow.

Figure 14:
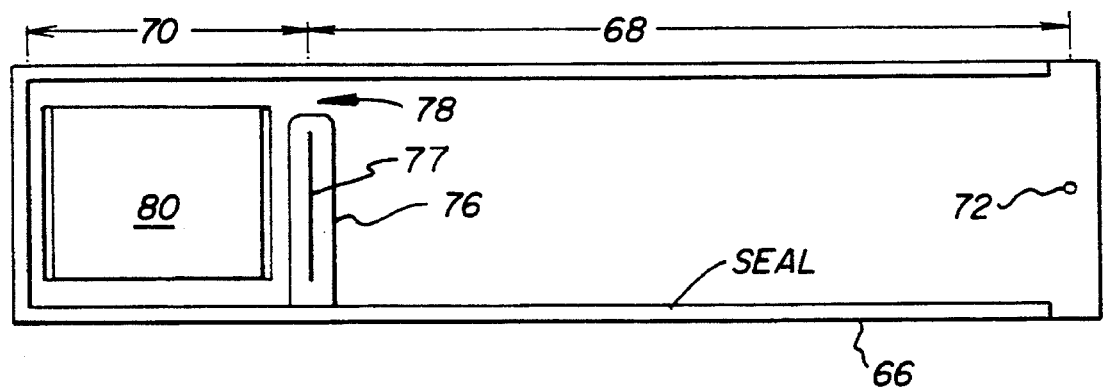
FIG. 14 is a top view of a pouch illustrating a further embodiment of the central seal.
Figure 15:
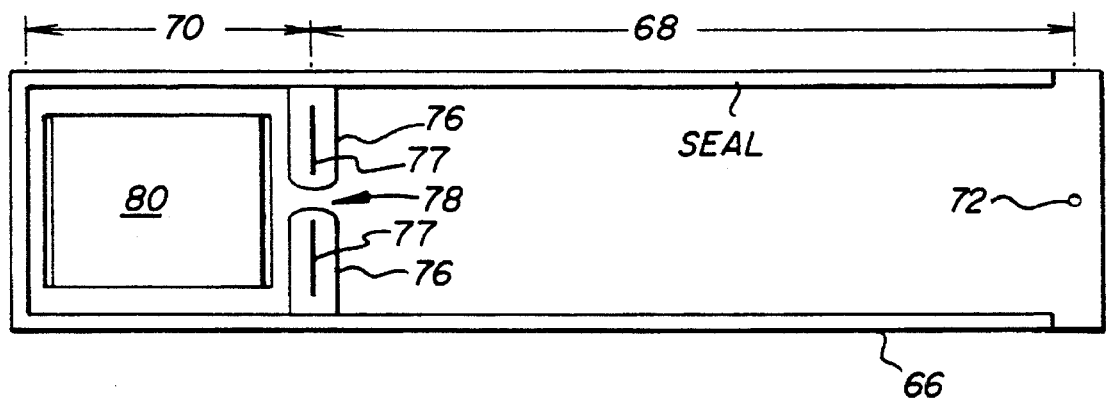
FIG. 15 is a top view of a pouch illustrating a still further embodiment of the central seal.

The invention has been described with reference to certain preferred embodiments thereof. It will be understood, however, that modifications and variations are possible within the scope of the appended claims. For example, the shape and configuration of the wiper fingers can be varied. The shield of the invention can also be separately incorporated and utilized with conventional sterilizer containers and pouches. The pouch of the invention can also be utilized with conventional shield structures. Finally, the central seal can be configured in different ways to provide the steam condensate slots 78. FIGS. 14 and 15, for example, respectively illustrate alternative embodiments where the central seal extends from both side edges of the pouch to provide a central steam/condensate slot, and the extension of the central seal from one side edge of the pouch to a location just short of the other side edge to provide a steam/condensate slot. In addition, the central seal can be formed without the slot. In such a case, the upwardly extending side edge portion of the shield portion would be deleted and the pouch would be fitted and retained in the container in the same manner as the prior art container described in PCT WO 93/18798. With the upwardly extending side edge portion removed, conventional pouches may also may employed in the container of the invention.

Industrial Utility

The invention can be utilized to sterilize medical instruments and other devices. The invention, however, is not limited to this particular application, and can also be employed in any application requiring that a microwave sensitive fluid be heated and applied to a component or mixed with another fluid as in a chemical reaction.

What is claimed is:

1. In a shielded microwave container used in conjunction with a pouch containing a sterilant aqueous liquid to sterilize dental instruments, the container comprising:
   a non-metallic holder comprising two portions hinged together along a respective first side edge of said portion, and a locking member at side edges of said portions opposite to said first side edges, said locking member being disposed so that, when locked, said portions define a volume between them, and
   a metal shield inside said holder and around said pouch, said shield comprising two shield portions that are adjacent when said holder is locked, each shield portion being mounted within one of said portions of said holder so that said shield portions occupy only a first part of said volume between said holder portions when locked, each of said shield portions including a dome curved outwardly away from the dome of said opposite shield portion, and a terminating side edge around the periphery of said dome,
   the improvement wherein said side edge of one of said shield portions includes along at least 85% of said side edge, means for maintaining metal-to-metal contact that is electrically conductive between said one shield portion side edge and said side edge of the other of said shield portions when said shield portions are moved apart to form a gap due to internal steam pressure within said pouch while maintaining the electrical conductivity.
   each said shield portion further including means defining at least one pre-formed fluid passageway into said shielded volume.

2. A container as defined in claim 1, wherein said shield portions are generally rectangular, with said side edge comprising two pairs of parallel edge portions, and wherein said contact-maintaining means are disposed along at least three of said four edge portions.

3. A container as defined in claim 1, wherein said contact-maintaining means are disposed along most of all of said four edge portions, so that at least 90% of said side edge of said one shield portion has said contact-maintaining means.

4. A container as defined in claim 1, wherein said contact-maintaining means comprise plural flexible electrically conductive resilient means for wiping along said at least 85% of said side edge, biased to wipe against said corresponding side edge of said other shield portion when said shield portions are brought into, or removed from, contact with each other, when said apparent gap is as large as 0.1 cm (40 mils).

5. A container as defined in claim 4, wherein said wiping means are repeated at a pitch of about 0.48 cm or less along said 85% of said side edge, so that metal-to-metal contact is maintained by a wiping action, even in the presence of dirt.

6. A container as defined in claim 1, wherein said passageway is formed in said side edge of each shield portion.

7. A container as defined in claim 6, wherein there are two of said passageways spaced apart.

8. A shield for use in a microwave container for steam-sterilizing a medical instrument, said shield comprising:
   a first and a second shield portion each having a domed center and a peripheral edge around said domed center, each peripheral edge being shaped to cooperate with the peripheral edge of the other of said shield portions to form a microwave choke, and a portion of said peripheral edge of one of said shield portions including along at least 85% of said portion of side edge, means for maintaining metal-to-metal contact that is electrically conductive between said one shield portion peripheral edge and said peripheral edge of the other of said shield portions when said shield portions are moved apart to form a gap due to internal steam pressure within said dome centers while maintaining the electrical conductivity, each of said shield portions further including means defining at least one preformed liquid access aperture into the volume defined by said domed centers when said peripheral edges form a microwave choke.

9. A shield as defined in claim 8, wherein said shield portions are generally rectangular, with said side edge comprising two pairs of parallel edge portions, and said contact-maintaining means are disposed along three of said four edge portions, and wherein at least one of said shield portions includes a pouch locating pin.

10. A shield as defined in claim 8, wherein said contact-maintaining means are disposed along most of all of said four edge portions, so that at least 90% of said peripheral edge of said one shield portion has said contact-maintaining means.

11. A shield as defined in claim 8, wherein said passageway is formed in said peripheral edge of each shield portion.

12. A shield as defined in claim 8, wherein said contact-maintaining means comprise plural flexible electrically conductive resilient means for wiping along said at least 85% of said side edge, biased to wipe against said corresponding peripheral edge of said other shield portion when said shield portions are brought into, or removed from, contact with each other, for gap widths of up to about 0.5 cm.

13. A shield as defined in claim 12, wherein said wiping means are repeated at a pitch of about 0.48 cm or less along said 85% of said portion of said peripheral edge, so that metal-to-metal contact is maintained by a wiping action, even in the presence of dirt.

* * * * *